United States Patent [19]

Marquardt et al.

[11] Patent Number: 4,731,439
[45] Date of Patent: Mar. 15, 1988

[54] SNAKE VENOM GROWTH ARRESTING PEPTIDE

[75] Inventors: Hans Marquardt, Mercer Island; George J. Todaro, Seattle; Daniel R. Twardzik, Bainbridge Island, all of Wash.

[73] Assignee: Oncogen, Seattle, Wash.

[21] Appl. No.: 801,019

[22] Filed: Nov. 22, 1985

[51] Int. Cl.$^4$ .................... A61K 37/02; C07G 7/00
[52] U.S. Cl. .................... 530/324; 530/350; 530/403; 530/405; 530/856; 514/12; 514/2; 514/21; 424/85
[58] Field of Search ............... 530/324, 325, 326, 856, 530/403, 405, 350; 514/12, 2, 21; 424/85, 86, 87

[56] References Cited

U.S. PATENT DOCUMENTS 4,220,722  9/1980  Rowley et al. ............... 530/403
4,221,777  9/1980  Nishino ....................... 530/405
4,340,535  7/1982  Voisin et al. ................. 424/85
4,500,637  2/1985  Neville, Jr. et al. .......... 530/403

OTHER PUBLICATIONS

Masuho et al., "Preparation of a Hybrid of Fragment Fab' of Antibody and Fragment A of Diphtheria Toxin and its Cytotoxicity", vol. 90, No. 1, 1979, Sep. 12, 1979, Biochem. and Biophys. Res. Comm., pp. 320–326.

Maeda et al., "Some Chemical Properties of the Venom of the Rattlesnake", *Crotalus Viridis Helleri*, Toxicon, vol. 16, pp. 431–441, 1978.

Laure, "Die Primärstruktur des Crotamins", Hoppe-Seyler's Z. Physiol. Chem. Bd. 356, S. 213–215, Feb. 1975.

Primary Examiner—Delbert R. Phillips
Assistant Examiner—Nathan M. Nutter
Attorney, Agent, or Firm—Bertram I. Rowland

[57] ABSTRACT

Novel cytotoxic agents are provided as small polypeptides related to a low molecular weight peptide derived from *Crotalus atrox*. The compounds may be used by themselves or in combination with other reagents, such as antibodies, for inhibiting cell growth.

8 Claims, No Drawings

SNAKE VENOM GROWTH ARRESTING PEPTIDE

BACKGROUND OF THE INVENTION

1. Field of the Invention

Toxic agents can find a variety of uses. Particularly, where the cytotoxic agent is specific or can be modified to be specific for particular strains or cell types, the cytotoxic agent can find use in eliminating a particular strain or cell type from a culture or tissue involving a plurality of different types of cells. For example, in the case of malignancies, it is desirable to be able to specifically eliminate the malignant cells, without serious mortality to the normal or healthy cells.

One source of toxins is snake venom. A number of toxins are known. However, there is still interest in finding additional toxins so as to increase the armamentarium of toxins available for use in particular applications. Toxins may vary in the immune response to the toxin, ease of coupling to other reagents, site of action of the toxin, and the like. To discover a new toxin from snake venom requires an assay of utility, extensive extractions, purification, and analysis to establish purity and amino acid sequence.

2. Description of the Relevant Literature

Cytotoxic peptides isolated from the venom of several species of rattlesnake have been sequenced, isolated and described. Myotoxin is derived from the venom of the prairie rattlesnake, Crotalus (Fox et al., *Biochemistry* (1979) 18:678-83); Crotamine derived from the venom of the South American rattlesnake, *Crotalus durissus terrificus* (Lauree and Hoppe-Seyler, *Physiol. Chem.* (1975) 356:213-15); and toxic peptide C derived from the venom of the Southern Pacific rattlesnake, *Crotalus viridis helleri* (Maeda et al., *Toxicon* (1978) 16:431-41).

SUMMARY OF THE INVENTION

Novel cytotoxic or cell growth arresting peptides are provided related to a peptide isolated from the venom of the Western Diamondback rattlesnake, *Crotalus atrox*. Conjugates of these peptides with specific binding members, e.g., ligands and receptors, may be used for selectively removing cells from a mixture of cells.

DESCRIPTION OF THE SPECIFIC EMBODIMENTS

Cytotoxic agents are provided comprising an approximately 6 kilodalton (kD) peptide isolated from the venom of *Crotalus atrox*, cytotoxic analogs thereof, and conjugates of the cytotoxic agents with peptides, particularly ligands and receptors for specific binding to a complementary binding member. The active moiety will have at least about 15 amino acids, usually at least about 25 amino acids, more usually at least about 35 amino acids, and not more than about 60 amino acids, more usually not more than about 50 amino acids. These active moieties may be joined to a wide variety of other compounds to be described subsequently.

The peptides of this invention will have the following formula:

$$pp^1 QC_1 aa^4 aa^5 aa^6 GGaa^9 C_2 aa^{11} aa^{12} aa^{13} aa^{14} C_3 aa^{16} aa^{17}$$

$$aa^{18} aa^{19} SDaa^{22} GKaa^{25} aa^{26} C_4 aa^{28} aa^{29} aa^{30}$$

$$WKC_5 C_6 Kaa^{36} aa^{37} aa^{38} aa^{39} pp^2$$

wherein:

$pp^1$ is the N-terminus and may be a hydrogen, a single amino acid, particularly a polar amino acid, more particularly an hydroxy substituted amino acid or basic amino acid, or a polypeptide of from 2-20, more usually from 2-10 amino acids, which may serve a variety of functions, such as a linking group, a modifying group, or the like;

$pp^2$ is the C-terminus and may be the terminal hydroxyl group, a single amino acid, particularly a polar amino acid, more particularly a carboxamido containing amino acid, or a polypeptide of from 2-20, more usually from 2-10 amino acids, which may serve the same functions as $pp^1$;

the individual letters have their normal meaning as part of the one-letter amino acid code, which is indicated below;

up to 5, usually not more than about 3, of the amino acids may serve as bonds, so as to be deletions in the structure;

$C_1$ with $C_5$, $C_2$ with $C_4$, and $C_3$ with $C_6$ form cysteine bridges, when cysteine bridges are present;

$aa^4$ is an aliphatic acidic or aromatic amino acid, particularly, D, E, H;

$aa^5$ is an aliphatic polar or basic amino acid, particularly carboxamido substituted or basic, more particularly N, Q, K, R;

$aa^6$ is an aliphatic charged amino acid, either acidic or basic, particularly D, E, K or R;

$aa^9$ is an aromatic amino acid, particularly F, H, W, Y;

$aa^{11}$ is an aliphatic charged amino acid, particularly basic amino acid, more particularly K, R;

$aa^{12}$ is an aromatic amino acid or aliphatic polar or charged amino acid, particularly acidic or neutral, more particularly hydroxy substituted as neutral, including F, H, W, Y, D, E, S, T;

$aa^{13}$ is an aliphatic non-polar or charged amino acid, particularly non-polar or basic, more particularly of from 4 to 6 carbon atoms, including L, I, V, K, R;

$aa^{14}$ is an aliphatic non-polar amino acid, particularly of from 4 to 6 carbon atoms, namely, L, I, V;

$aa^{16}$ is an aliphatic non-polar amino acid of from 4 to 6 carbon atoms, particularly P, I, L, V;

$aa^{17}$ is an aliphatic non-polar or polar amino acid of from 3 to 5 carbon atoms, particularly hydroxy substituted when polar, more particularly S, T, A, P, V;

$aa^{18}$ is an aliphatic charged or non-polar amino acid, particularly basic when charged, and of from 3 to 6, usually 4 to 6 carbon atoms, particularly P, I, L, V, K, R;

$aa^{19}$ is an aliphatic polar amino acid of from 3 to 4 carbon atoms, particularly hydroxy substituted, more particularly S, T;

$aa^{22}$ is an aliphatic non-polar or aromatic amino acid, when aliphatic being of from 5 to 6 carbon atoms, particularly F, I, L, V;

$aa^{25}$ is an aliphatic neutral amino acid, of from 3 to 6 carbon atoms, particularly of from 4 to 6 carbon atoms being polar or non-polar, when polar having a sulfur atom, more particularly M, I, L, V;

$aa^{26}$ is an aliphatic charged or non-polar amino acid, when polar particularly acidic, of from 2 to 5, usually of from 2 to 4 carbon atoms, more particularly G, A, P, D, E;

$aa^{28}$ is an aliphatic charged amino acid of from 4 to 6 carbon atoms, which may be basic or acidic, particularly D, E, K, R;

$aa^{29}$ is an aliphatic or aromatic amino acid, when aliphatic of from 3 to 5 carbon atoms, particularly A, P, V, F, H, W, Y;

$aa^{30}$ is an aliphatic neutral non-polar or basic amino acid, when neutral non-polar being of from 4 to 6, usually 5 to 6 carbon atoms, particularly I, L, V, K, R;

$aa^{36}$ is an aliphatic basic amino acid, particularly K, R;

$aa^{37}$ is an aliphatic or aromatic amino acid, when aliphatic being of from 2 to 3 carbon atoms, particularly G, A, F, H, W, Y;

$aa^{38}$ is an aliphatic neutral polar or non-polar amino acid, of from 2 to 4 carbon atoms, when polar being particularly hydroxy substituted, more particularly being G, A, P, S, T;

$aa^{39}$ is an aliphatic non-polar amino acid of from 2 to 6 carbon atoms, particularly of from 2 to 3 carbon atoms, particularly G, A, P, I, L, V.

The groups for the various amino acids and the one-letter designations are indicated as follows:

| aliphatic | |
|---|---|
| neutral | |
| non-polar | G,A,P,V,I,L |
| polar | S,T,M,C,N,Q |
| charged | |
| acidic | D,E |
| basic | K,R |
| aromatic | F,H,W,Y |
| G - glycine | N - asparagine |
| A - alanine | Q - glutamine |
| P - proline | D - aspartic acid |
| V - valine | E - glutamic acid |
| I - isoleucine | K - lysine |
| L - leucine | R - arginine |
| S - serine | F - phenylalanine |
| T - threonine | H - histidine |
| M - methionine | W - tryptophan |
| C - cysteine | Y - tyrosine |

Of particular interest are peptides of the following formula:

```
              F  R  L L
   S Q C E Q E G G    C  F
              H  K  V I

P   T  I     L
   C   SR  SD  G K    G C E P L W K C C K
      L   S   L    M

R
     W G G
   K
``` wherein:
when two amino acids are indicated at the same site, either one may be present at that site, but it is preferred that those amino acids above the line go together and those amino acids below the line go together.

It is to be further understood that conservative substitutions are permissible. By conservative substitutions are intended that the following amino acids on the same line may be substituted one for the other.

G, A
V, I, L
D, E
K, R
S, T
F, H, W, Y

The N-terminus of the peptide may be blocked or unblocked, blocking usually involving an aliphatic acid, e.g., acetic acid or formic acid, alkylation, etc. The subject compounds are found to be heat- and acid-stable under test procedures described in the Experimental section.

Of particular interest is the naturally occurring growth arresting peptide which is at least about 90%, preferably 95%, more preferably 99% pure. It can be used by itself or in combination with other toxins.

The subject cytotoxic or growth-inhibiting compounds may be conjugated to a wide variety of ligands and receptors by conventional techniques. The functional groups involved in linking may be a variety of acid groups, such as carboxyl, sulfonyl, and phosphoryl, combinations of thiol and olefins, dithio, aldehydes, azo groups, diazo groups, or the like. For the most part, difunctional compounds will be employed, which can be reacted stepwise, although difunctional compounds which react simultaneously may also be used. Illustrative reagents include glutaraldehyde, formaldehyde, para-maleimidobenzoic acid, methyldithioacetic acid, diazobenzoic acid, or the like. The particular manner which is employed for linking the cytotoxic moiety to a specific binding member is not critical to this invention.

Specific binding members will be ligands and receptors, where the specific binding members serve to provide specific binding to a particular target. For example, cells will normally have surface antigens and receptors which are characteristic of a particular cell type. Thus, by use of appropriate ligands or receptors conjugated to the toxic agent, the toxic agent can be preferably directed to those cells having the reciprocal specific binding member.

Various compounds which may be used as ligands include steroids, low-density lipoprotein, growth factors, viral proteins, etc. By contrast, either natural receptors or preferably immunoglobulins or their fragments may be employed, where the receptors are directed to specific surface antigens. The immunoglobulins of interest include IgA, IgD, IgM, IgE, and IgG, preferably IgG, including any one of the subtypes. The immunoglobulins may be derived from any convenient source, particularly mouse or human. The immunoglobulins may be derived from hybridomas, from transformed cells, e.g., EBV transformed lymphocytes, or by recombinant DNA technology. Particularly, mouse variable regions may be joined to human or other host constant region to provide for chimeric immunoglobulins which may provide for lower antigenicity. In addition, the whole immunoglobulin need not be used, but rather fragments thereof, such as Fab, F(ab')$_2$, Fv, or the like.

The ligand and toxin may be joined by links which are stable in the target cell or unstable, so that the toxin and targetting reagent may be separated in the cell. Desirably, the toxin will be endocytosed, so as to effect its action intracellularly. Where the targetting agent does not detrimentally affect the toxic activity of the toxin, there will be no need to have a cleavable linkage. Where a cleavable linkage is desired, conveniently a disulfide linkage may be employed, which may be reduced in the host cell.

The conjugates may involve a wide variety of ratios between the targetting agent, the specific binding member, and the toxin. Usually, there will be at least one toxin per targetting agent, but not more than about one toxin per 0.5 kilodaltons (kD) of targetting agent. Usually, there will be at least one toxin molecule per 100 kD of targetting agent, more usually at least one per 50 kD of targetting agent. Where the targetting agent is small, such as a low molecular weight hapten, there may be 2 or more ligands per toxin, usually not more than about 5 ligands per toxin.

The subject compounds can be used in vitro or in vivo. For in vitro use, they can be used for selectively destroying cells which can be distinguished from other cells in a culture or in tissue. The subject compounds can be added to the medium in amounts sufficient to destroy the undesired cells. For example, in detecting particular histocompatibility antigens, one may add reagents containing antibodies specific for the particular histocompatibility antigen. By adding a dye which will only be absorbed by dead cells, the presence of the dye in the cells will be indicative of the particular histocompatibility type. The amount of toxin targetted reagent may be varied widely and will be optimized for particular situations in in vitro use. Too much of the toxin targetted reagent should not be used so as to result in non-specific binding and false positives, while too little should not be used, which could result in false negatives due to a low level of binding, which cannot be readily detected.

For in vivo use, the conjugate may be administered parenterally or by injection, particularly intravenously. The amount of the conjugate employed will vary widely, depending upon the nature of the cell which is to be killed, the extent of the cell population, the resistance of the cell to the conjugate, the effectiveness of the conjugate, and the like. When administered at other than a specific site, usually, the amount of protein will vary from about 1 µg to 10 mg, usually up to 2 mg, per kilogram of host body weight. At a specific site, the amount of protein will be in the lower portion of the concentration range. The conjugate can be administered in a physiologically acceptable medium, such as phosphate buffered saline, saline, or other convenient vehicle. As powders, the conjugate may be compounded with other materials which may provide for directing the composition to a particular organ, protracted release, or the like. The manner in which proteinaceous compositions may be administered to a host finds ample exemplification in the prior art and will not be discussed in further detail.

Of particular interest as target cells are tumor cells and pathogenic microorganisms. Of particular interest because of their widespread occurrence are lung carcinomas; colon and rectal cancer cells; breast cancer; uterine carcinoma; prostatic carcinoma; bladder and kidney cancer; lymphoma; leukemia; and Hodgkins disease.

Illustrative of pathogenic microorganisms are protozoa, such as *Plasmodium vivas*, *P. maleriae*, *P. ovale*, and *P. falciparum*, Gram-negative bacteria, such as Pseudomonas, Klebsiella, and Neisseria, Gram-positive bacteria, and the like.

EXPERIMENTAL

Materials and Methods

Purification of Growth Arresting Peptide from the Venom of *Crotalus atrox*.

The crude peptide compound was obtained by milking venom from *Crotalus atrox* and clarified by low speed centrifugation prior to lyophilization. Freeze-dried venom was dissolved (10 mg/ml) in 1M acetic acid and insoluble material removed by low speed centrifugation.

Initial purification was achieved by applying the sample in 7.5 ml quantities to a Bio-Gel P10 column equilibrated with 1M acetic acid and fractions were collected (3.5 ml) and aliquots were removed and lyophilized. Aliquots were initially tested for inhibition of DNA synthesis in A549 human lung carcinoma cell cultures. Briefly, $2 \times 10^4$ A549 cells were seeded in 96-well plates and after attachment the cells were treated with appropriate column fractions. Five days later, wells were pulsed with $^{125}$I deoxyuridine and DNA synthesis measured relative to control wells based on $^{125}$I-deoxyuridine incorporation. Two major peaks of inhibition were seen. A first peak of low molecular weight inhibitory activity eluting near the 6,000$M_r$ insulin marker was further purified utilizing high pressure liquid chromatography (HPLC).

The sample was lyophilized and resuspended in 0.05% trifluoroacetic acid (TFA) in HPLC grade purified water (Water's Associates). Insoluble material was removed by centrifugation and the sample was injected into a $C_{18}$-Novapak column. The sample was eluted with a linear gradient of 20 to 60% acetonitrile in 0.05% TFA at a flow rate of 1 ml/min at 22° C. Each $A_{214}$ absorbing peptide was collected separately and aliquots tested for inhibition of DNA synthesis. The peptide eluting at 54% acetonitrile inhibited DNA synthesis of A549 cells; no inhibition was seen using other column fractions. SDS-PAGE of this activity indicated a single silver-staining band; no other bands were visualized on this gel, suggesting that the peptide has been purified to homogeneity.

Inhibited Cell Morphology

Inhibited cells demonstrated a striking morphological change 24 hr after treatment with this peptide which is designated as "Growth Arresting Peptide" (GAP). Both human tumor cells and non-transformed fibroblasts were inhibited in this assay (50% of cells seeded) at a peptide concentration of approximately 100 ng/ml. Cells post treatment became round and most dendrite-like protrusions were noticeably absent; cells however still adhered to the plate. This effect was irreversible as washing treated cells and refeeding with fresh media containing 10% serum did not permit cells to recover to their original phenotype.

Chemical Structure of GAP

The amino acid sequence of GAP was determined by microsequence analysis of peptides obtained from enzymatic digests of reduced and S-carboxamidomethylated GAP with (a) the endoproteinase Lysine-C; (b) TPCK-trypsin (L-(1-tosylamido-2-phenyl)ethylchloromethyl ketone); and, (c) *Staphylococcal aureus* V8. The peptide fragments were purified by reverse phase HPLC, using volatile solvents. Amino terminally blocked peptides were incubated in 12N HCl at ambient temperature for 16 hr. Samples were then dried by lyophilization. The peptides were subjected to automated Edman degradation in the model 470A gas phase Protein Sequencer (Applied Biosystems, Inc.). The phenylthiohydantion amino acids were analyzed by rpHPLC.

The amino acid sequence of GAP is as follows:

S Q C E Q E G G F C R F L L C P S R T S D I G K L

G C E P L W K C C K R W G G

The structure was determined by microsequence analysis. Briefly, GAP was reduced with dithiothreitol, S-carboxamidomethylated with iodoacetamide, and a 10% aliquot subjected to automated Edman degradation. No N-terminal amino acid was detected, even when several cycles of Edman degradation were performed, suggesting that the terminal amino group of GAP is blocked.

A 45% aliquot of S-carboxamidomethylated GAP was digested with Lysine-C enzyme. Peptides K1–24 and K25–32 were separated by rpHPLC. Peptides K33–35 and K36–39 were not retained by the column and were eluted as a mixture. No attempt was made to purify these peptides. A 50% aliquot of peptides K1–24 and K25–32, respectively, were subjected to automated Edman degradation. No N-terminal amino acid was detected when K1–24 was sequenced. The remaining 50% aliquot of K1–24 was subsequently digested with TPCK-trypsin. The tryptic peptides T1–11, T12–18 and T19–24 were separated by rpHPLC and subjected to Edman degradation. No N-terminal amino acid was detected when a 50% aliquot of peptide T1–11 was sequenced, suggesting that T1–11 is the N-terminal peptide of K1–24. The remaining 50% aliquot of T1–11 was subsequently deblocked with 12N HCl and the sequence of acid-treated T1–11 was determined. T12–18 contained a C-terminal arginine residue, whereas K1–24 contained a C-terminal lysine residue and was thus assumed to be the carboxyl-terminal peptide of K1–24. Peptide K25–32 was completely sequenced. The presented data support the proposed amino acid sequence of GAP from residues 1–32.

The remaining 45% aliquot of S-carboxamidomethylated GAP was digested with *Staphylococcal aureus* V8. Peptides E1–6, E7–21 and E22–39 were separated by rpHPLC. A 50% aliquot of peptides E1–6, E7–21 and E22–39 were subjected to automated Edman degradation. No N-terminal amino acid was detected for peptide E1–6. The complete sequences of E7–21 and E22–39 extended the proposed structure of GAP from residues 1–39 and confirmed the assignments made for peptides T12–18, T19–24 and K25–32. A 50% aliquot of peptide E1–6 was subsequently deblocked with 12N HCl, possibly through an acid catalyzed N-O acetyl shift at Ser-1. The sequence of acid-treated E1–6 was determined. The possibility remained that additional peptides might be present in the structure beyond residue Gly-39, since no carboxypeptidase treatment of GAP confirmed Gly-39 as C-terminal amino acid. However, the extensive sequence homology between GAP and Crotamine, Myotoxin A and Toxic peptide C lends credence to the proposed structure.

Structurally, GAP belongs to the rattlesnake toxin family, a group of polypeptides causing muscle degeneration by damaging the endoplasmic reticulum as the primary target. Comparison of the GAP with all protein sequences stored in the Protein Sequence Database (PIR Release 5.0, May 1985) did not reveal any extensive homology with any other known sequence. The sequences of GAP and the rattlesnake toxins can be aligned so that cysteine residues display homologous positions by inserting two deletions between residues 10 and 11 of GAP. The presence of six half-cystine residues in GAP suggest three disulfide bridges in the polypeptide. The above indicated amino acid sequence can be widely varied as to amino acid sequence while retaining the conformational structure and cytotoxic activity.

The subject toxins can be used in place of such toxins as ricin, diptheria toxin, abrin and the like in accordance with known methodology. See, for example, Jansen et al., Recept.-Mediated Binding Intern. Toxins Horm. [Proc. Symp.] 1980 (Pub. 1981) 351–356 (C.A. 95:126185u); Masuho et al., *Biochem. Biophys. Res. Comm.* (1979) 90:320–326; U.S. Pat. No. 4,340,535.

Although the foregoing invention has been described in some detail by way of illustration and example for purposes of clarity of understanding, it will be obvious that certain changes and modifications may be practiced within the scope of the appended claims.

What is claimed is:

1. A toxic peptide conjugate comprising a toxic peptide of the formula:

$$pp^1QC_1aa^4aa^5aa^6GGaa^9C_2aa^{11}aa^{12}aa^{13}aa^{14}C_3aa^{16}aa^{17}$$

$$aa^{18}aa^{19}SDaa^{22}GKaa^{25}aa^{26}C_4aa^{28}aa^{29}aa^{30}$$

$$WKC_5C_6Kaa^{36}aa^{37}aa^{38}aa^{39}pp^2$$

wherein:
  $pp^1$ is the N-terminus and is hydrogen, or an amino acid chain of from 1–20 amino acids;
  $pp^2$ is the C-terminus and may be a hydroxyl, or an amino acid chain of from 1–20 amino acids;
  the individual letters have their normal meaning as provided in the one-letter amino acid code;
  up to five of the amino acids designated with numbers may serve as bonds;
  when cysteine bridges are present, $C_1$ pairs with $C_5$, $C_2$ with $C_4$, and $C_3$ with $C_6$;
  $aa^4$ is an aliphatic acidic or aromatic amino acid;
  $aa^5$ is an aliphatic polar or basic amino acid;
  $aa^6$ is an aliphatic charged amino acid;
  $aa^9$ is an aromatic amino acid;
  $aa^{11}$ is an aliphatic basic amino acid;
  $aa^{12}$ is an aromatic amino acid or aliphatic polar or charged amino acid;
  $aa^{13}$ is an aliphatic non-polar or charged amino acid;
  $aa^{14}$ is an aliphatic non-polar amino acid;
  $aa^{16}$ is an aliphatic non-polar amino acid of from 4 to 6 carbon atoms;
  $aa^{17}$ is an aliphatic non-polar or polar amino acid of from 3 to 5 carbon atoms;
  $aa^{18}$ is an aliphatic non-polar or basic amino acid of from 3 to 6 carbon atoms;
  $aa^{19}$ is an aliphatic polar amino of from 3 to 4 carbon atoms;
  $aa^{22}$ is an aliphatic non-polar or aromatic amino acid;
  $aa^{25}$ is an aliphatic neutral amino acid of from 3 to 6 carbon atoms;
  $aa^{26}$ is an aliphatic charged or non-polar amino acid of from 2 to 5 carbon atoms;
  $aa^{28}$ is an aliphatic charged amino acid of from 4 to 6 carbon atoms;

$aa^{29}$ is an aliphatic amino acid of from 3 to 5 carbon atoms or an aromatic amino acid;

$aa^{30}$ is an aliphatic non-polar or basic amino acid of from 4 to 6 carbon atoms;

$aa^{36}$ is an aliphatic basic amino acid;

$aa^{37}$ is an aliphatic amino acid of from 2 to 3 carbon atoms or an aromatic amino acid;

$aa^{38}$ is an aliphatic neutral amino acid of from 2 to 4 carbon atoms; and $aa^{38}$ is an aliphatic neutral amino acid of from 2 to 4 carbon atoms; and $aa^{39}$ is an aliphatic non-polar amino acid, wherein the N-terminus may be blocked or unblocked, covalently bonded to a member of a specific binding pair.

2. A toxic peptide conjugate according to claim 1, wherein said member of said specific binding pair is a ligand.

3. A toxic peptide conjugate according to claim 1, wherein said member of said specific binding pair is a receptor.

4. A toxic peptide conjugate according to claim 3, wherein said receptor is an antibody.

5. A toxic peptide conjugate comprising a toxin from *Crotalus atrox* venom covalently linked to a specific binding pair member.

6. A toxic peptide conjugate according to claim 1, wherein the covalent bonding between the toxic peptide and the member of a specific binding pair involves an acid, thiol, olefin, dithio, aldehyde, azo, or diazo functional group in forming said covalent bonding.

7. A toxic peptide conjugate according to claim 1, wherein said toxic peptide is covalently bonded to said member of a specific binding pair by a direct bond or a difunctional compound.

8. A toxic peptide conjugate according to claim 1, wherein said covalent bonding employs a difunctional compound selected from the group consisting of glutaraldehyde, formaldehyde, maleimidobenzoic acid, methyldithioacetic acid, or diazo benzoic acid.

* * * * *